(12) United States Patent
Fitzgerald et al.

(10) Patent No.: US 10,895,490 B2
(45) Date of Patent: *Jan. 19, 2021

(54) HYDROGEN PEROXIDE RESERVOIR ASSEMBLY INCLUDING A FLOAT POSITION SENSOR FOR DETERMINING LIQUID LEVEL

(71) Applicant: Scholle IPN Corporation, Northlake, IL (US)

(72) Inventors: Sean Fitzgerald, West Dundee, IL (US); Christopher Zaro, Arlington Heights, IL (US)

(73) Assignee: Scholle IPN Corporation, Northlake, IL (US)

( * ) Notice: Subject to any disclaimer, the term of this patent is extended or adjusted under 35 U.S.C. 154(b) by 133 days.

This patent is subject to a terminal disclaimer.

(21) Appl. No.: 15/860,981

(22) Filed: Jan. 3, 2018

(65) Prior Publication Data

US 2019/0204136 A1    Jul. 4, 2019

(51) Int. Cl.
| | | |
|---|---|---|
| *G01F 23/76* | (2006.01) | |
| *G01F 23/68* | (2006.01) | |
| *G05D 9/00* | (2006.01) | |
| *A61L 2/20* | (2006.01) | |
| *A61L 2/18* | (2006.01) | |
| *G01F 1/00* | (2006.01) | |

(52) U.S. Cl.
CPC .............. *G01F 23/76* (2013.01); *G01F 23/686* (2013.01); *G05D 9/00* (2013.01); *A61L 2/186* (2013.01); *A61L 2/208* (2013.01); *A61L 2202/15* (2013.01); *A61L 2202/23* (2013.01); *G01F 1/007* (2013.01)

(58) Field of Classification Search
CPC ........ G01F 23/76; G01F 23/68; G01F 23/686; G01F 23/2962; G01F 1/007; F16K 37/005; Y10T 137/8342; G05D 9/00; A61L 2/186; A61L 2/208; A61L 2202/15; A61L 2202/23

See application file for complete search history.

(56) References Cited

U.S. PATENT DOCUMENTS 4,379,434 A * 4/1983 Thordarson ............. G01F 23/62
116/110
5,258,146 A * 11/1993 Almquist ................ B29C 41/12
264/401

(Continued)

*Primary Examiner* — Harshad R Patel
*Assistant Examiner* — Nigel H Plumb
(74) *Attorney, Agent, or Firm* — The Watson IP Group, PLC; Jovan N. Jovanovic (57) ABSTRACT

A reservoir assembly comprising a lower manifold, an upper manifold, a reservoir body, a float member and a sensor system. The upper manifold has an upper cover placed over a central bore, and sealingly engaged therewith, the upper cover being at least partially transparent. The reservoir body has a lower end sealingly engaged with the lower manifold and the upper end sealingly engaged with the upper manifold. The float member is positioned within the reservoir and can slidably move between the upper and lower manifolds. The float member has an upper target that is substantially parallel to an upper cover positioned on the upper manifold. The sensor system has a float position sensor positioned over the upper cover and targeting the upper target of the float member to, in turn, determine the position of the float member relative to the float position sensor.

20 Claims, 8 Drawing Sheets

(56) References Cited

U.S. PATENT DOCUMENTS

| | | | |
|---|---|---|---|
| 5,706,857 A * | 1/1998 | Dowling, Jr. | B67D 7/3227 |
| | | | 137/202 |
| 5,743,138 A * | 4/1998 | Cheng | G01F 1/22 |
| | | | 73/305 |
| 8,402,822 B2 * | 3/2013 | Hopper | G01F 23/0046 |
| | | | 73/313 |
| 8,431,077 B2 * | 4/2013 | Goncalves | A61L 2/208 |
| | | | 422/28 |
| 9,354,102 B2 * | 5/2016 | Zaro | G01F 23/2962 |
| 9,605,991 B2 * | 3/2017 | Montfort | G01F 23/76 |
| 2007/0255458 A1 * | 11/2007 | Haslem | B67D 7/061 |
| | | | 700/282 |
| 2010/0163567 A1 * | 7/2010 | Chiang | A47G 23/16 |
| | | | 220/703 |
| 2013/0340889 A1 * | 12/2013 | Neimark | B01F 13/1055 |
| | | | 141/95 |
| 2017/0356408 A1 * | 12/2017 | Yang | F02M 37/0047 |

* cited by examiner

HYDROGEN PEROXIDE RESERVOIR ASSEMBLY INCLUDING A FLOAT POSITION SENSOR FOR DETERMINING LIQUID LEVEL

CROSS-REFERENCE TO RELATED APPLICATION

N/A

BACKGROUND OF THE DISCLOSURE

1. Field of the Disclosure

The disclosure relates in general to sanitizing equipment, and more particularly, to a hydrogen peroxide reservoir assembly. Typically, although not required, such sanitizing equipment is well suited for use in the sanitizing and/or cleaning of receptacles (i.e., rigid and flexible packaging) prior to filling. For example, and not limited thereto, the sanitizing equipment is well suited for use in association with an aseptic filler.

2. Background Art

The use of level sensors for measuring the quantity of fluid in a reservoir, as well as flow rates is well known in the art. In the area of sanitizing fluids, such as hydrogen peroxide, it is important to be able to measure flow rates into, for example, sanitizing equipment, to insure that proper sanitization is occurring therein.

Problematically, hydrogen peroxide is a fluid wherein relatively small flow rates can be difficult to properly determine. One solution is shown in U.S. Pat. No. 9,354,102 issued to Zaro and assigned to Scholle IPN Corporation, the complete specification of which is hereby incorporated by reference in its entirety. Such a solution is advantageous over prior solutions, as the solution enabled the measuring of flow rates for use in aseptic fillers and to measure relatively low flow rates.

Nevertheless, improvement is desired. Specifically, due to the relative sizing of the device, along with the float construction and the construction of the device, greater accuracy than can be delivered by such a device is desired. In addition, the limits of the sensors had been reached, and inherent limitations in the construction of the apparatus limit improvement in the readability of the sensor and the determination of the flow rate.

SUMMARY OF THE DISCLOSURE

The disclosure, in an aspect to a reservoir assembly comprising a lower manifold, an upper manifold, a reservoir body, a recirculation valve, a float member and a sensor system. The lower manifold has a body with a central bore defined therein. The lower manifold has at least one inlet and at least one outlet. The upper manifold has a body with a central bore defined therein and substantially corresponding to the central bore of the lower manifold in a spaced apart positioning. The upper manifold has an upper cover placed over the central bore, and sealingly engaged therewith. The upper cover being at least partially transparent. The reservoir body has a lower end sealingly engaged with the central bore of the lower manifold and an upper end sealingly engaged with the central bore of the upper manifold. The reservoir body is substantially uniform in cross-sectional configuration. The float member is positioned within the reservoir and is structurally configured to slidably move between the upper and lower manifolds within the reservoir body. The float member has an upper target that is substantially parallel to the upper cover. The sensor system has a float position sensor comprising a laser sensor. The float position sensor is positioned over the upper cover and targeting the upper target of the float member to, in turn, determine the position of the float member relative to the float position sensor.

In some configurations, the assembly further has a manifold locating and coupling system extending between the upper manifold and the lower manifold, securing the relative position of the upper and lower manifolds to each other.

In some configurations, the manifold locating and coupling system further includes a plurality of rods extending between and coupled to each of the upper manifold and the lower manifold.

In some configurations, the reservoir body has a substantially circular cross-sectional configuration.

In some configurations, the central bore further includes a step in portion spaced apart from an upper surface and a lower surface of the upper manifold, defining a lower end flange and an upper end flange. The upper cover is sealingly engaged with the upper end flange. The reservoir body is sealingly engaged with the lower end flange.

In some configurations, the upper manifold includes at least one overflow port in communication with the central bore of the upper manifold, wherein the port is defined within the step in portion.

In some configurations, the lower manifold further includes a reservoir body portion and a fluid movement portion. The reservoir body engages the reservoir body portion. The at least one inlet and the at least one are outlet defined in the fluid movement portion.

In some configurations, the fluid movement portion further includes a drain port extending therefrom.

In some configurations, the float member further comprises a central region with an upper frustoconical structure extending in the direction of the upper manifold. The upper frustoconical structure terminates at the upper target.

In some configurations, the central region comprises a substantially cylindrical member having a plurality of flat surfaces disposed substantially parallel to the direction of travel of the float member within the reservoir.

In some configurations, the flat surfaces comprise four flat surfaces that are spaced apart from each other at 90° intervals.

In some configurations, the float member further comprises a plurality of slots extending along the central region positioned between adjacent flat surfaces and disposed substantially parallel to the direction of travel of the float member within the reservoir.

In some configurations, the float member further comprises a lower conical structure extending from the central region toward the lower manifold.

In some configurations, the upper target comprises a substantially circular member having a target diameter, with the target diameter being between one third and one fourth a diameter of the reservoir body.

In some configurations, the float member comprises an upper member and a lower member. The upper member includes an inner bore, with the lower member sealingly engaging the upper member so as to effectively seal the inner bore.

In some configurations, the sensor system further includes a low level sensor and a high level sensor spaced apart from each other. The low level sensor is positioned between the high level sensor and the lower manifold. The high level sensor is positioned between the low level sensor and the upper manifold.

In another aspect of the disclosure, the disclosure is directed to a reservoir assembly comprising a lower manifold, an upper manifold, a reservoir body, a float member and a sensor system. The lower manifold has a body at least one inlet and at least one outlet. The upper manifold has a body with a central bore defined therein. The upper manifold has an upper cover placed over the central bore, and sealingly engaged therewith. The upper cover is at least partially transparent. The reservoir body has a lower end sealingly engaged with the lower manifold and an upper end sealingly engaged with the central bore of the upper manifold. The reservoir body is substantially uniform in cross-sectional configuration. The float member is positioned within the reservoir. The float member is structurally configured to slidably move between the upper and lower manifolds within the reservoir body. The float member has an upper target that is substantially parallel to the upper cover. The sensor system has a float position sensor positioned over the upper cover and targeting the upper target of the float member to, in turn, determine the position of the float member relative to the float position sensor.

In some configurations, the sensor comprises a laser sensor.

In some configurations, the assembly further includes a manifold locating and coupling system coupling the lower manifold and the upper manifold together, and retaining the reservoir body therebetween.

In some configurations, the manifold locating and coupling system further comprises a plurality of rods extending between and coupled to each of the upper manifold and the lower manifold.

BRIEF DESCRIPTION OF THE DRAWINGS

The disclosure will now be described with reference to the drawings wherein.

DETAILED DESCRIPTION OF THE DISCLOSURE

While this disclosure is susceptible of embodiment in many different forms, there is shown in the drawings and described herein in detail a specific embodiment(s) with the understanding that the present disclosure is to be considered as an exemplification and is not intended to be limited to the embodiment(s) illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
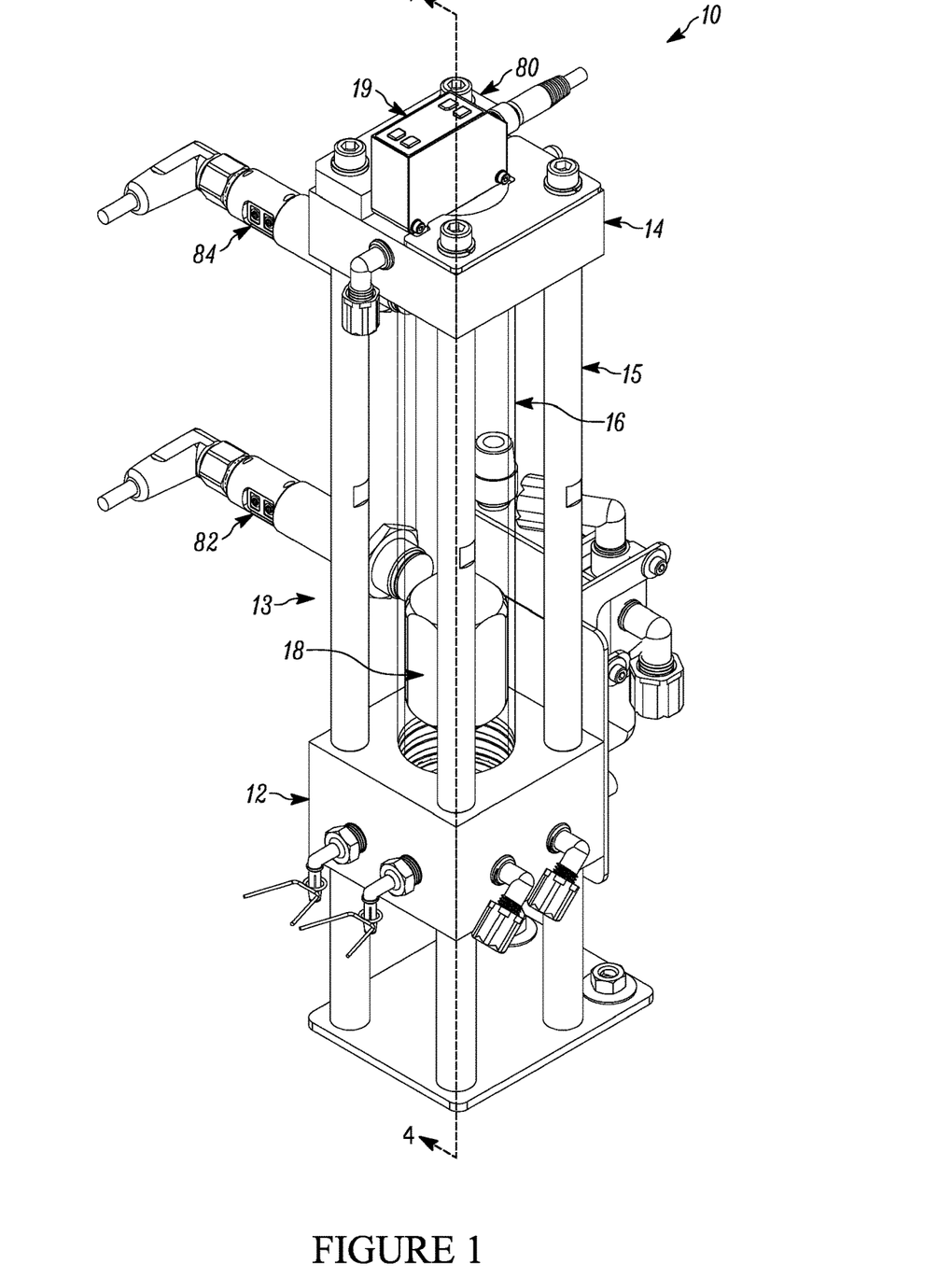
FIG. 1 of the drawings is a first perspective view of the assembly of the present disclosure.
Figure 2:
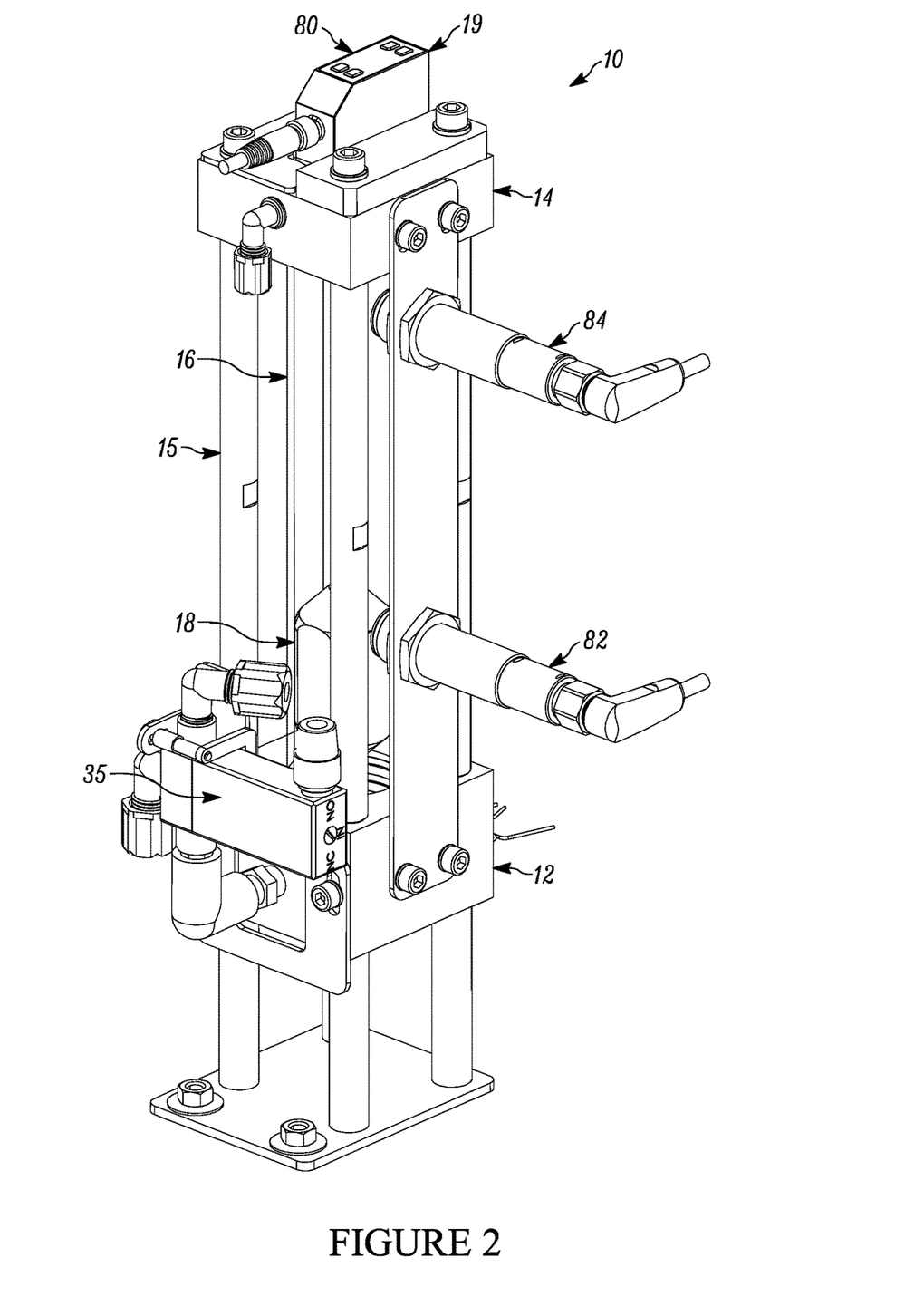
FIG. 2 of the drawings is a second perspective view of the assembly of the present disclosure.
Figure 3:
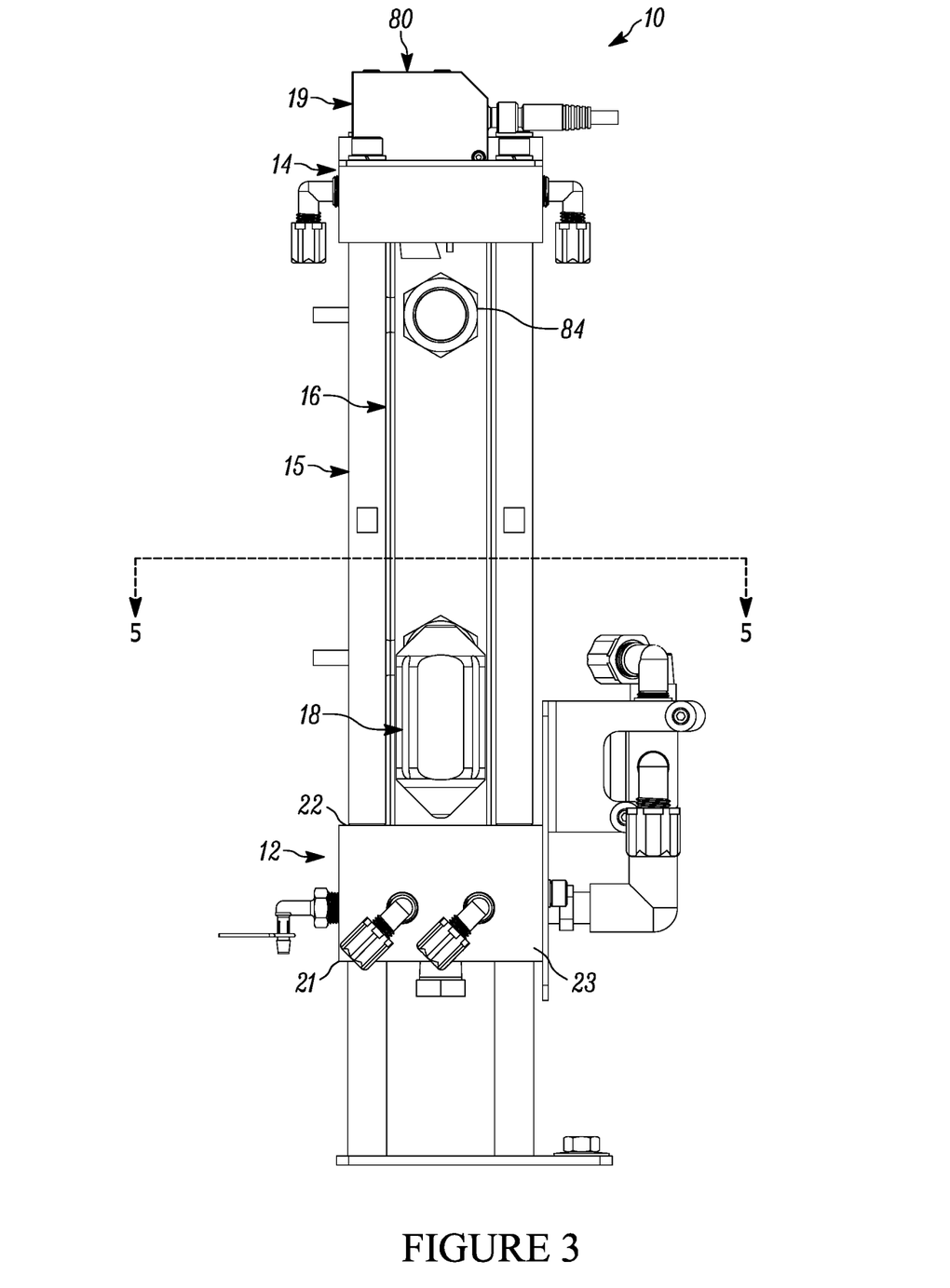
FIG. 3 of the drawings is a side elevational view of the assembly of the present disclosure.
Figure 4:
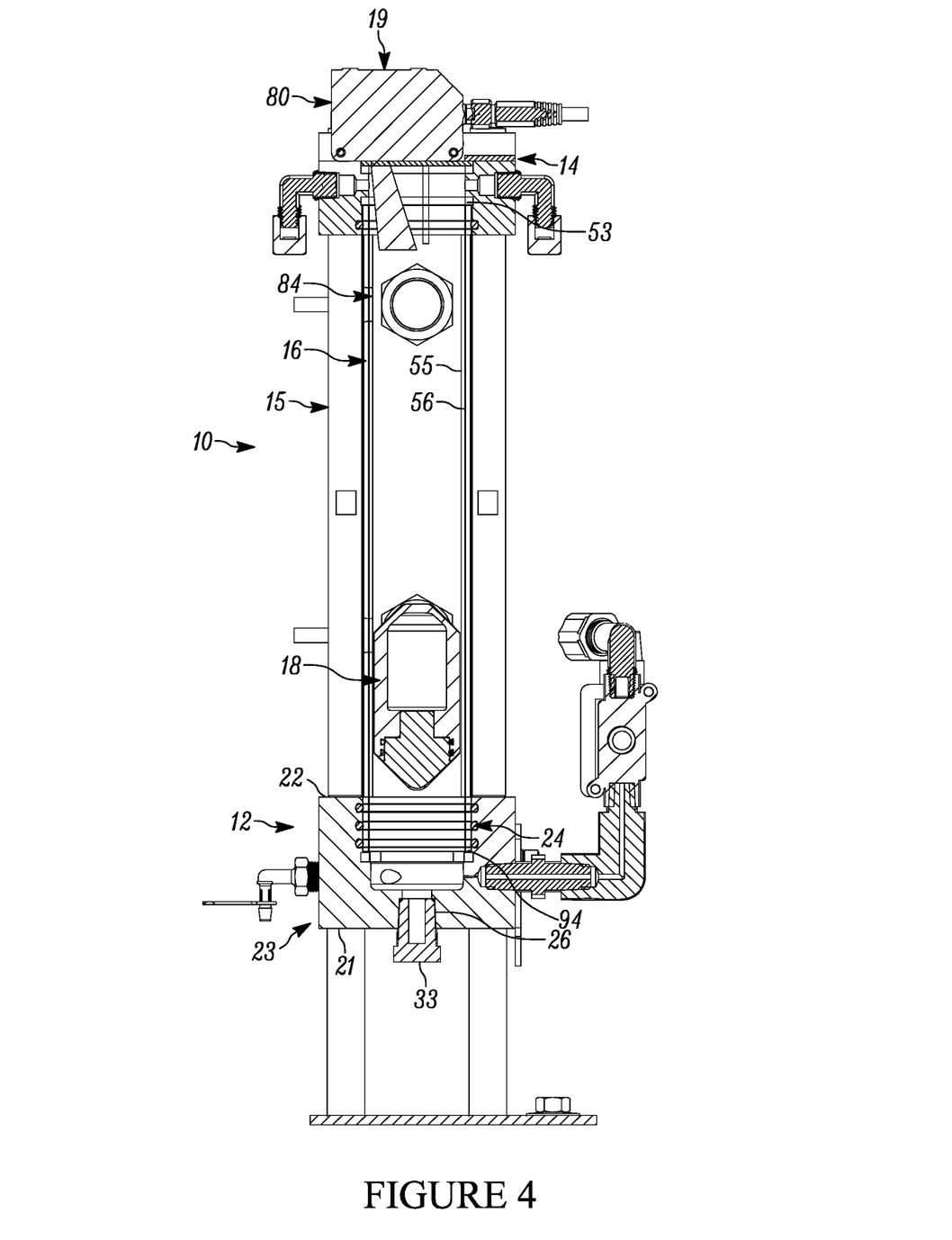
FIG. 4 of the drawings is a cross-sectional view of the assembly of the present disclosure, taken generally about lines 4-4 of FIG. 1.
Figure 5:
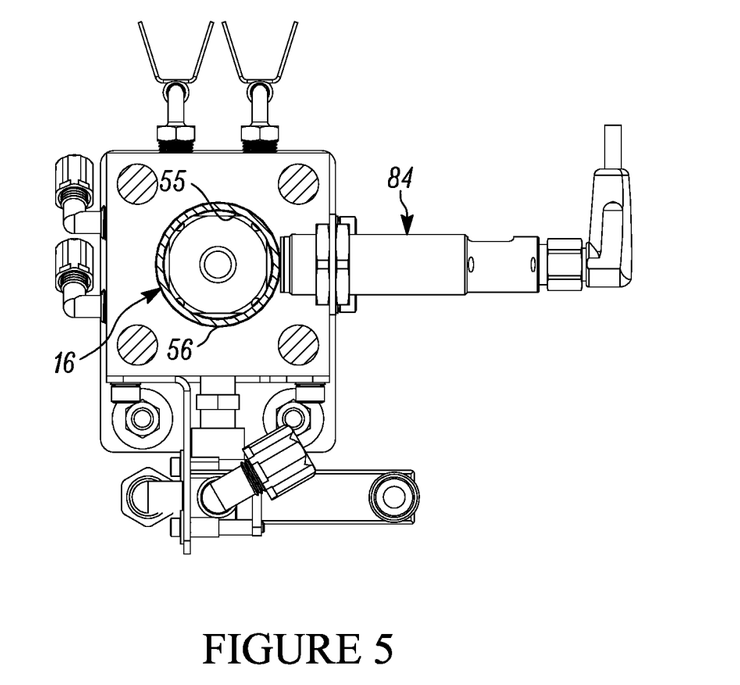
FIG. 5 of the drawings is a cross-sectional view of the assembly of the present disclosure, taken generally about lines 5-5 of FIG. 3.

Referring now to the drawings and in particular to FIG. 1, the disclosure is directed to a hydrogen peroxide reservoir assembly shown generally at 10. The hydrogen peroxide reservoir is used in association with a disinfecting, sanitizing or cleaning system that is preferably coupled to a filler for rigid or flexible packaging (such as, for example, pouches, bags or the like). The particular system, as well as the particular filler with which the assembly can be coupled is not limited to any particular system, with the understanding that any such system requires the use of carefully metered hydrogen peroxide liquid. While the assembly is configured and primarily intended for use in association with hydrogen peroxide solutions, it is not specifically limited thereto. It will be understood that while reference is made to hydrogen peroxide, the use of the reservoir can be with other liquids and solutions, without limitation.

Figure 6:
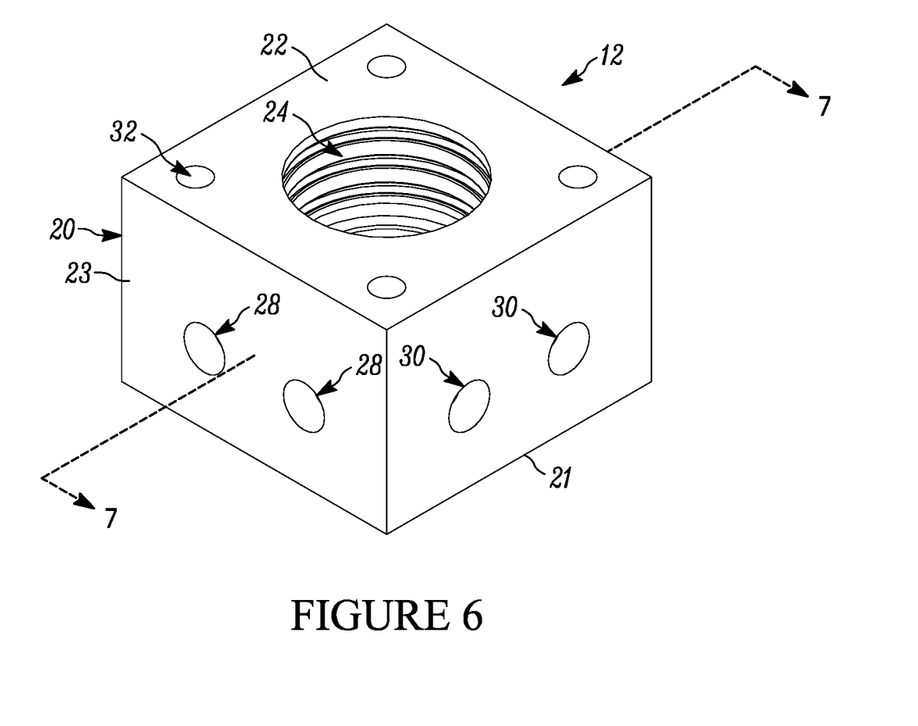
FIG. 6 of the drawings is a perspective view of the lower manifold of the assembly of the present disclosure.
Figure 7:
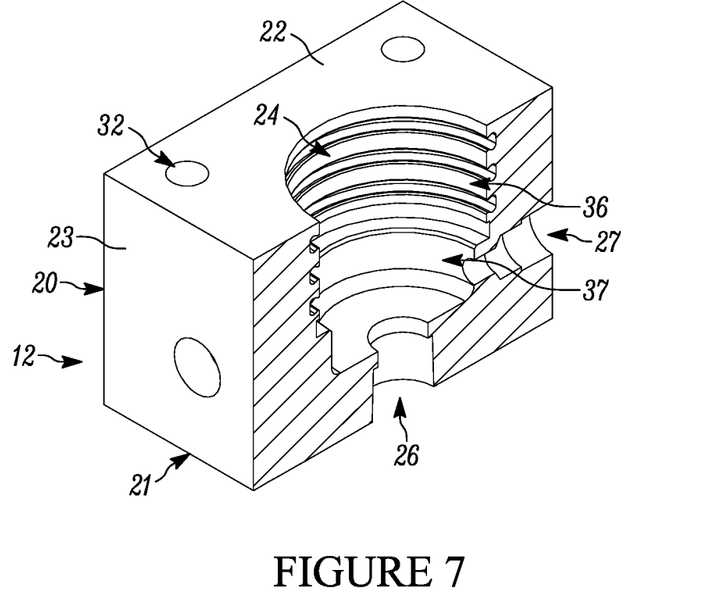
FIG. 7 of the drawings is a cross-sectional view of the lower manifold of the assembly of the present disclosure, taken generally about lines 7-7 of FIG. 6.

In the configuration shown, the hydrogen peroxide reservoir assembly 10 includes lower manifold 12, upper manifold 14, manifold locating and coupling rods 15, reservoir body 16, float member 18 and sensor system 19. The lower manifold 12 is shown in FIGS. 6 and 7 as comprising a body 20 defining a generally rectangular cubic (although other shapes are contemplated) structure having lower surface 21, upper surface 22 and side surfaces 23. In other configuration, other shapes, having, for example, generally flat upper and lower surfaces with a cross-section that may be circular, oval, polygonal or arbitrary are likewise contemplated, as well as upper and lower surfaces that are other than planar, and other than parallel, for example. In the configuration shown, the cross-sectional configuration, and the upper and lower surfaces are substantially square or rectangular.

The body 20 includes a central bore 24 that extends inwardly from the upper surface 22 and is substantially a right cylindrical cross-sectional configuration. In the configuration shown, the central bore extends toward the lower surface, stopping short thereof. The central bore, in the configuration shown, may include a reservoir body portion 36 and a fluid movement portion 37. A flange may be disposed between the reservoir body portion and the fluid movement portion, such that the cross-sectional configuration of the fluid movement portion may be smaller than the cross-sectional configuration of the reservoir body portion. The reservoir body portion may further include annular recesses and the like to accommodate sealing o-rings or the like. A drain bore 26 extends from the central bore to the lower surface 21, which drain bore may be threaded. A drain plug 33 may be threadedly engaged with the drain bore so as to provide a sealing interface therebetween.

A plurality of bores are defined in the body 20 which communicate, preferably, with the fluid movement portion 37 of the central bore 24. In particular, these bores include the fill inlet bore 27, which can be coupled to a fluid supply as well as a valve 35 through a series of fittings and the like, a pair of outlet bores 28 (or more), a pair of recirculation inlets 30 (or more). It will be understood that in the configuration shown, the system includes a plurality of separate metering systems and dispensing systems, with each requiring its own recirculation inlet and outlet bores. Other systems may combine these features or may include further bores that provide communication with the central bore.

A plurality of mounting openings 32 or bores are defined on the upper and lower surfaces, which provide for attachment points to other mounting equipment. Additional bores may be positioned on the side surfaces for the same purpose. It will be understood that the particular manner of attachment of the assembly is not limited to the configuration shown. In the configuration shown, the base is supported by four lower coupling rods and a base plate. The base plate is positioned below and spaced apart from the lower surface of the body. The four lower coupling rods are positioned proximate the corners and provide for coupling and spacing of the two components. The base plate can be coupled to an outside surface, with the lower coupling rods providing for access to the drain plug 33. It is contemplated that other structures may be utilized for mounting while providing access to the drain plug.

The upper manifold 14 is shown in FIG. 1 as comprising body 40, upper cover 42 and clamping members 44. The body 40, although not required, has a similar rectangular cubic configuration that has a cross-sectional configuration that substantially matches that of the body 20 of the lower manifold 12. The body 40 includes lower surface 46, upper surface 47 and side surfaces 48. The side surfaces 48 do not have the height of the side surfaces of 23, in the configuration shown, which renders the volume of the upper manifold smaller than the volume of the lower manifold. Of course, variations are contemplated. As with the lower manifold, the upper manifold includes a central bore 50 that substantially matches the central bore 24.

Figure 8:
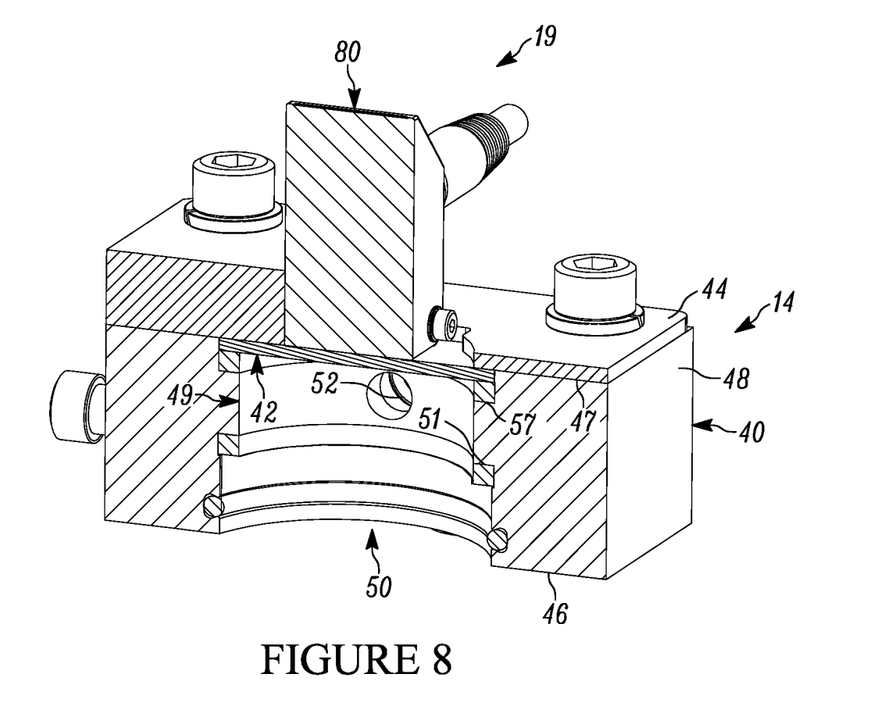
FIG. 8 of the drawings is a cross-sectional view of the upper manifold of the assembly of the present disclosure.

In the configuration shown, the central bore 50 extends completely through the body, that is from the lower surface to the upper surface. The central bore has a central step in portion 49 of reduced cross-sectional configuration, defining a lower end flange 51 and an upper end flange 57. A pair of overflow bores 52, 52' are disposed on opposite side surfaces and extend into the central bore 50 at the step in portion. These overflow bores are configured to receive fittings which can remove fluid from within the reservoir in the event that there is an overflow situation. The lower portion below the step in flange may include one or more annular recesses so as to accommodate O-rings and the like.

The upper cover comprises a transparent member that is configured to fit into the region above the step in portion and which rests upon the upper end flange 57 (in sealed engagement with a sealing ring member (such as a flexible ring). In the configuration shown, as reliability and readability of the float position sensor is of strict importance, the upper cover comprises a transparent quartz crystal member. Of course, other configurations may utilize a glass or transparent polymer, such as a polycarbonate or the like. It will be understood that the upper cover may be partially transparent and partially opaque or translucent.

The clamping members 44 comprise a plurality of plates that can be coupled to the upper surface 47 of the body of the upper manifold 14. The clamping members are configured to sandwich the upper cover 42 to the body 40. Additionally, and as will be explained, the clamping members may also provide for a coupling mechanism by which to couple the float position sensor 80 of the sensor system 19. The plates can cover the entirety of the upper surface (absent the location for the float position sensor), or, alternatively, the plates can leave portions of the upper cover unobstructed to allow for visual review and/or inspection.

The manifold locating and coupling system 13 comprises rods 15 that are shown in FIG. 1 as comprising four rods that extend into corresponding bores in the upper surface 22 of the body 20 of the lower manifold 12 and the lower surface 46 of the body 40 of the upper manifold 14. In the configuration shown, the rods are positioned at or near each corner and a total of four rods are presented. The rods may include threaded ends which can be threaded into correspondingly threaded bores. In other configurations, the rods may be coupled through an interference fit. In still other configurations, other means of coupling the upper and lower manifold (as well as to locate the same) can be utilized without departing from the scope of the present disclosure. In other configurations plates or other structures may be utilized for locating and coupling the lower manifold and the upper manifold.

The reservoir body 16 is shown in FIG. 1 as comprising a substantially elongated tubular member, of substantially uniform cross-sectional configuration. In the configuration shown, the elongated tubular member is of a transparent material, such as glass, or a polymer. The reservoir body 16 includes upper end 53, lower end 54 and includes inner surface 55 and outer surface 56. The reservoir body 16 is configured so that when the upper manifold and the lower manifold are attached together. The upper end 53 sealingly engages the lower end flange 51 (with the aid of a suitable flexible O-ring or the like). Additionally, O-rings sealingly engage the outer surface 56 to seal against the same, while remaining sealed within the annular recesses of the central bore 50.

At the same time, the lower end 54 sealingly engages with the reservoir body portion 36 through O-rings disposed within the annular recesses engaging with the outer surface 56 as well as the engagement of the lower end 54 with the reservoir portion of the central bore 24 at the flange through a suitable flexible member. Indeed, the manifold locating and coupling rods, when fully coupled, provide just enough pressure on the reservoir body so as to create the seal at both the lower end and the upper end thereof.

In the configuration shown, the inner diameter of the reservoir body 16 is 32.9 mm, with an outside diameter of 37.4 mm. Such a reservoir size allows for a quick response for the float, as the volume of the reservoir body is such that, at typical usage rates, the float will respond and be measurably differently oriented within a few seconds.

Figure 9:
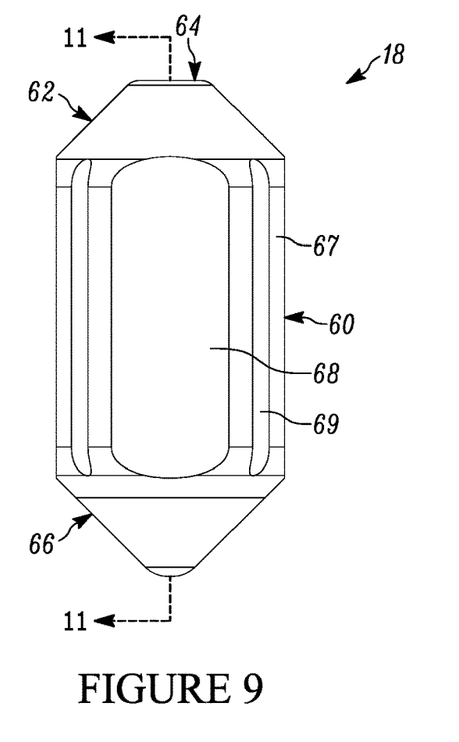
FIG. 9 of the drawings is a side elevational view of the float member of the assembly of the present disclosure.
Figure 10:
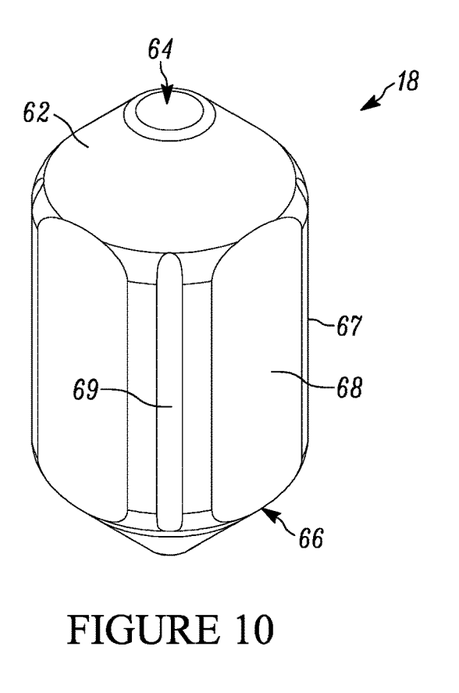
FIG. 10 of the drawings is a perspective view of the float member of the assembly of the present disclosure.

The float member 18 is shown in FIG. 1 as comprising a central region 60, an upper frustoconical structure 62, a upper target 64 and a lower conical structure 66. The float member is structurally configured to slidably move between the lower manifold and the upper manifold, with the understanding that the float member, due to refilling and the amount filled, may never actually reach the upper or the lower manifold. The central region 60 includes a generally cylindrical configuration having a plurality of flat surfaces 68 and a plurality of slots 69. Both the flat surfaces and the plurality of slots extend along the length of the central region, and are generally parallel to each other. The central region is sized so that the cylindrical portion substantially matches the configuration of the inner surfaced 55 with a slight spacing to allow for the float member to slidably move along the inner surface of the reservoir body between the upper and lower ends. In the configuration shown, there are a total of four flat surfaces disposed equidistant from each other with a slot extending between adjacent flat surfaces (i.e., the flat surfaces comprise four flat surfaces that are spaced apart from each other at 90° intervals). The central region is longer than either one of the upper frustoconical structure 62 and the lower conical structure 66.

The upper frustoconical structure 62 extends from the upper end of the central region and comprises a right frustoconical structure. The upper target 64 is spaced at the upper end of the float member so as to be substantially perpendicular to the travel of the float member within the reservoir body, and substantially parallel to the upper cover 42 of the upper manifold 14. In the configuration, the diameter of the upper target is less than approximately one-fourth of the diameter of the central region 60. In other configurations, the diameter of the upper target may be larger or smaller than the foregoing, however, it has been found that, generally, a diameter that is between one-fifth and one-third of the diameter of the central region provides a suitable surface against which the sensor can take measurements.

The lower conical structure 66 is a substantial mirror image of the upper frustoconical structure, with the exception that the lower conical structure is a full conical structure (with a rounded end, in some configuration), whereas the upper structure is frustoconical. Such a structure aids in the centering of the float member as the float member remains within the reservoir body. As will be understood, it is desirable to minimize any lateral movement and rotational movement is an axis other than a longitudinal axis that extends through the center of the central region from the upper structure to the lower structure, to, in turn, maintain the upper target in a configuration wherein it is substantially parallel with the upper cover 44 of the upper manifold.

Figure 11:
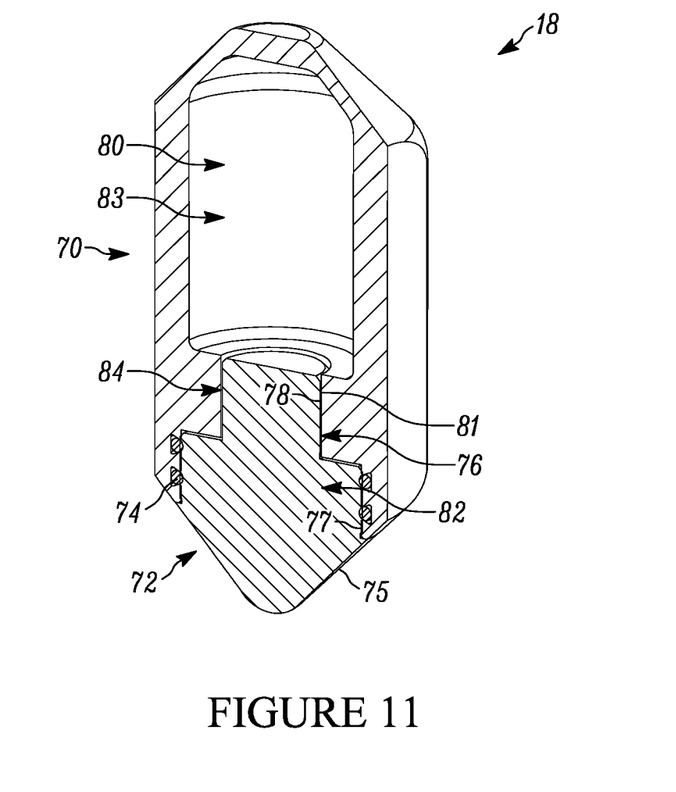
FIG. 11 of the drawings is a cross-sectional view of the float member of the assembly of the present disclosure, taken generally about lines 11-11 of FIG. 9.

The float member is constructed from two separate components that are coupled together, namely, the upper member 70 and the lower member 72. Each member may be molded from a polymer member, or another material, or materials. For example, the upper member 70 may comprise a material that is different from the lower member and, a reflective surface may be formed or positioned at the upper target. The different materials may have different densities, or may have different constructions. In one example, the upper material may have a density that is, for example, lower than the density of the lower material. Additionally, the material of one or both may be heavier than the fluid, as there is further an air pocket which may make the reservoir body float. Preferably, and as will be explained, the float member is at least partially submerged within the hydrogen peroxide solution.

The upper member 70, in the configuration shown, includes inner bore 80 that defines an open inner space. A inward protrusion 82 is disposed within the inner bore 80 which separates the inner bore into an upper chamber 83 and a lower chamber 82. The inward protrusion generally defines the protrusion passage 84. The lower chamber includes a plurality of annular recesses that are configured to retain O-rings or other sealing members. The upper member, in the configuration shown comprises an integrally molded and monolithic member, although co-molded members, and other structures are likewise contemplated (including structures that are not molded, but otherwise formed and from materials other than a polymer based material). In the configuration shown, the upper member forms the central region 60, the upper frustoconical structure 62 and the upper target 64.

The lower member 72 is shown as comprising lower body portion 75 and inner body portion 76. The lower body portion 75 includes interfacing surface 77 along with the surface that forms the lower conical structure 66. The interfacing surface 77 structurally corresponds in configuration to the lower chamber 82 of the upper member 70. The protrusion interfacing surface 78 extends upwardly and structurally corresponds in configuration to the protrusion passage 84 of the upper member 70. As will be understood, when the upper and the lower members are matingly engaged, the lower member sealingly engages with the upper member about at least one of the interfacing surface and the protrusion interfacing surface, with the O-rings 74 providing sealing engagement along the interfacing surface 77. As can be seen, the upper chamber 83 of the upper member 70 remains open and generally air or another fluid is captured therewithin. For example, air can remain trapped within the upper chamber 83 so as to affect the buoyancy of the float member. Additionally, other fluids (gasses, liquids), gels, semi-solids or solids can likewise bet trapped within the upper chamber of the upper member 70.

The sensor system 19 is shown in FIG. 1 as comprising float position sensor 80, low level sensor 82 and high level sensor 84. The low and high level sensors 82, 84 are positioned on a plate that is coupled to each of the upper and the lower manifolds 12, 14. The sensors are a secondary check to determine if the float member is at or near the maximum or minimum levels. The float position sensor 80 comprises a laser distance sensor, which typically operates in a range of 50 mm to 150 mm. In the configuration shown, the sensor comprises a laser distance sensor, available from Sick AG of Waldkirch, Germany under the Part Number 6050513. Of course, other laser distance sensors are contemplated for use. While a laser distance sensor is highly accurate, any instability in the float member can register incorrect readings, and with rotational movement, the upper target may be incorrectly positioned to reflect back the laser, which, in turn, precludes measurement, or decreases accuracy thereof.

In operation, it is necessary to determine the flow rate, and to determine if the flow rate is commensurate with the process requirements. For example, if the flow rate determined is outside of the upper and lower process limits, sterility may be lost. Furthermore, pump speeds and other process rates can be altered if a deviation in the flow rate is determined.

In an embodiment of the present disclosure, it is contemplated that the sensor samples every four seconds. As such, over five readings, at one reading every four seconds will provide a total of five readings in a 16 second time window. From this number of samples, a flow rate can be determined in any number of units (i.e., ml/minute; grams/minute, etc.). That is, in the configuration that is provided, with a stable float member in a properly sized reservoir body, a sampling of one reading every four seconds can provide the data necessary to determine a flow rate. In the configuration shown, the system can provide a 25% loss or gain in a configuration wherein readings are taken every four seconds. It is contemplated that in the present disclosure, the flow rate, for example, could be approximately 9.00 grams per minute. Such a flow rate would be difficult to calculate with accuracy in the systems of the prior art, at the desired sampling rate and based on calculations that are performed based upon samples taken at the prescribed intervals. It is contemplated that in such a configuration, the reservoir when filled includes approximately 75 grams of fluid.

Measurement accuracy is increased through the use of the recirculation valve 35 by elimination of large air pockets within the hydrogen peroxide supply lines. Large air bubbles entering the reservoir would compromise the buoyancy of the float. The recirculation valve is contemplated to activate for 5 seconds with flow through the valve and back to the supply container. The reservoir is filled after the recirculation cycle.

The foregoing description merely explains and illustrates the disclosure and the disclosure is not limited thereto except insofar as the appended claims are so limited, as those skilled in the art who have the disclosure before them will be able to make modifications without departing from the scope of the disclosure.

What is claimed is:

1. A reservoir assembly comprising:
a lower manifold having a body with a central bore defined therein, the lower manifold having at least one inlet and at least one outlet;
an upper manifold having a body with a central bore defined therein and substantially corresponding to the central bore of the lower manifold in a spaced apart positioning, the upper manifold having an upper cover placed over the central bore thereof, and sealingly engaged therewith, the upper cover being at least partially transparent;
a reservoir body having a lower end sealingly engaged with the central bore of the lower manifold and an upper end sealingly engaged with the central bore of the upper manifold, the reservoir body being substantially uniform in cross-sectional configuration;
a float member positioned within the reservoir, the float member structurally configured to slidably move between the upper and lower manifolds within the reservoir body, the float member having an upper target that is substantially parallel to the upper cover; and
a sensor system having a float position sensor comprising a laser distance sensor, the float position sensor positioned over the upper cover and targeting the upper target of the float member to, in turn, determine the position of the float member relative to the float position sensor.

2. The reservoir assembly of claim 1 further comprising a manifold locating and coupling system extending between the upper manifold and the lower manifold, securing the relative position of the upper and lower manifolds to each other.

3. The reservoir assembly of claim 2 wherein the manifold locating and coupling system further includes a plurality of rods extending between and coupled to each of the upper manifold and the lower manifold.

4. The reservoir assembly of claim 1 wherein the reservoir body has a substantially circular cross-sectional configuration.

5. The reservoir assembly of claim 1 wherein the central bore further includes a step in portion spaced apart from an upper surface and a lower surface of the upper manifold, defining a lower end flange and an upper end flange, with the upper cover sealingly engaged with the upper end flange, and the reservoir body being sealingly engaged with the lower end flange.

6. The reservoir assembly of claim 5 wherein the upper manifold includes at least one overflow port in communication with the central bore of the upper manifold, wherein the port is defined within the step in portion.

7. The reservoir assembly of claim 1 wherein the lower manifold further includes a reservoir body portion and a fluid movement portion, with the reservoir body engaging the reservoir body portion and with the at least one inlet and the at least one outlet defined in the fluid movement portion.

8. The reservoir assembly of claim 7 wherein the fluid movement portion further includes a drain port extending therefrom.

9. The reservoir assembly of claim 1 wherein the float member further comprises a central region with an upper frustoconical structure extending in the direction of the upper manifold, with the upper frustoconical structure terminating at the upper target.

10. The reservoir assembly of claim 9 wherein the central region comprises a substantially cylindrical member having a plurality of flat surfaces disposed substantially parallel to the direction of travel of the float member within the reservoir.

11. The reservoir assembly of claim 10 wherein the flat surfaces comprise four flat surfaces that are spaced apart from each other at 90° intervals.

12. The reservoir assembly of claim 10 wherein the float member further comprises a plurality of slots extending along the central region positioned between adjacent flat surfaces and disposed substantially parallel to the direction of travel of the float member within the reservoir.

13. The reservoir assembly of claim 9 wherein the float member further comprises a lower conical structure extending from the central region toward the lower manifold.

14. The reservoir assembly of claim 9 wherein the upper target comprises a substantially circular member having a target diameter, with the target diameter being between one third and one fourth a diameter of the reservoir body.

15. The reservoir assembly of claim 1 wherein the float member comprises an upper member and a lower member, the upper member including an inner bore, with the lower member sealingly engaging the upper member so as to effectively seal the inner bore.

16. The reservoir assembly of claim 1 wherein the sensor system further includes a low level sensor and a high level sensor spaced apart from each other, the low level sensor positioned between the high level sensor and the lower manifold, and the high level sensor positioned between the low level sensor and the upper manifold.

17. A reservoir assembly comprising:
a lower manifold having a body at least one inlet and at least one outlet;
an upper manifold having a body with a central bore defined therein, the upper manifold having an upper cover placed over the central bore, and sealingly engaged therewith, the upper cover being at least partially transparent;
a reservoir body having a lower end sealingly engaged with the lower manifold and an upper end sealingly engaged with the central bore of the upper manifold, the reservoir body being substantially uniform in cross-sectional configuration;
a float member positioned within the reservoir, the float member structurally configured to slidably move between the upper and lower manifolds within the reservoir body, the float member having an upper target that is substantially parallel to the upper cover; and
a sensor system having a float position sensor positioned over the upper cover and targeting the upper target of the float member to, in turn, determine the position of the float member relative to the float position sensor.

18. The reservoir assembly of claim 17 wherein the sensor comprises a laser distance sensor.

19. The reservoir assembly of claim 17 further comprising a manifold locating and coupling system coupling the lower manifold and the upper manifold together, and retaining the reservoir body therebetween.

20. The reservoir assembly of claim 19 wherein the manifold locating and coupling system further comprises a plurality of rods extending between and coupled to each of the upper manifold and the lower manifold.

* * * * *